(12) United States Patent
Subramanyam et al.

(10) Patent No.: US 9,561,193 B2
(45) Date of Patent: Feb. 7, 2017

(54) ORAL AND SKIN CARE COMPOSITIONS BASED ON A 3,3-DIALKYL-1,1-BIPHENYL-2,2-DIOL OR A 3,3-DIALKENYL-1,1-BIPHENYL-2,2-DIOL

(75) Inventors: Ravi Subramanyam, Belle Mead, NJ (US); Neelima Utgikar, Maharashtra (IN); Guofeng Xu, Plainsboro, NJ (US); Ying Yang, Monmouth Junction, NJ (US); Lin Fei, Kendall Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 260 days.

(21) Appl. No.: 14/343,940

(22) PCT Filed: Sep. 8, 2011

(86) PCT No.: PCT/US2011/050795
§ 371 (c)(1),
(2), (4) Date: Mar. 10, 2014

(87) PCT Pub. No.: WO2013/036229
PCT Pub. Date: Mar. 14, 2013

(65) Prior Publication Data
US 2014/0234232 A1   Aug. 21, 2014

(51) Int. Cl.
| | |
|---|---|
| *A61K 31/05* | (2006.01) |
| *A61K 8/34* | (2006.01) |
| *A61Q 11/00* | (2006.01) |
| *A61Q 17/00* | (2006.01) |
| *A61Q 19/10* | (2006.01) |
| *A61Q 15/00* | (2006.01) |

(52) U.S. Cl.
CPC .............. *A61K 31/05* (2013.01); *A61K 8/347* (2013.01); *A61Q 11/00* (2013.01); *A61Q 17/005* (2013.01); *A61Q 19/10* (2013.01); *A61K 2800/5922* (2013.01); *A61Q 15/00* (2013.01)

(58) Field of Classification Search
USPC ......................................................... 424/49
See application file for complete search history.

(56) References Cited

U.S. PATENT DOCUMENTS

| | | | |
|---|---|---|---|
| 5,776,435 A | 7/1998 | Gaffar et al. | |
| 6,031,061 A | 2/2000 | Suh et al. | |
| 6,500,409 B1 | 12/2002 | Scherl et al. | |
| 2005/0239903 A1* | 10/2005 | Harper | A61K 31/05 514/721 |
| 2006/0140880 A1 | 6/2006 | Subramanyam et al. | |
| 2007/0048235 A1 | 3/2007 | Harmalker et al. | |
| 2008/0233058 A1 | 9/2008 | Maitra et al. | |
| 2009/0087501 A1 | 4/2009 | Cummins | |
| 2009/0311200 A1 | 12/2009 | Lambert et al. | |
| 2011/0059029 A1 | 3/2011 | Kohli et al. | |

FOREIGN PATENT DOCUMENTS

| | | | |
|---|---|---|---|
| WO | WO01/82922 | * 11/2001 | ............. A61K 31/05 |
| WO | WO 2006/107451 | 10/2006 | |
| WO | WO 2011/106492 | 9/2011 | |

OTHER PUBLICATIONS

Seo et al., 1986, "Antimicrobial Activities of Hydroxybiphenyl Derivatives(II)," Arch. Pharm. Res. 9(3):127-130.
Alexakis et al., 2004, "Biphenol-Based Phosphoramidite Ligands for the Enantioselective Copper-Catalyzed Conjugate Addition of Diethylzinc," J. Org. Chem. 69(17):5660-5667.
Bae et al., 1986, "Antimicrobial Activities of Hydroxybiphenyl Derivatives," Database CAPlus AN: 1986:568755.
International Search Report and Written Opinion in International Application No. PCT/US2011/050795, mailed Jun. 14, 2012.
Li et al., 2003, "Allylmagnolol, a Novel Magnolol Derivative As Potent Antioxidant," Bioorg. Med. Chem. 11:3665-3671.
Written Opinion in International Application No. PCT/US2011/050795, mailed Aug. 9, 2013.

* cited by examiner

*Primary Examiner* — Walter Webb

(57) ABSTRACT

Described herein are compositions comprising antibacterially effective amounts of a compound of Formula (I): or a salt thereof in which R1 and R2 are each independently (C1-C6) alkyl or (C2 C6) alkenyl, and a carrier. Suitable carriers include orally acceptable carriers and dermatologically acceptable carriers. The disclosed compositions include oral care and personal care compositions useful for treating or preventing oral and skin conditions, respectively.

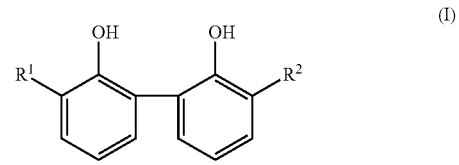

(I)

16 Claims, No Drawings

ORAL AND SKIN CARE COMPOSITIONS BASED ON A 3,3-DIALKYL-1,1-BIPHENYL-2,2-DIOL OR A 3,3-DIALKENYL-1,1-BIPHENYL-2,2-DIOL

BACKGROUND

There is an ongoing need for antibacterial agents and compositions comprising the same, which have efficacy against common oral bacteria and skin bacteria.

SUMMARY

In some embodiments, the present invention provides a composition comprising a compound of Formula (I)

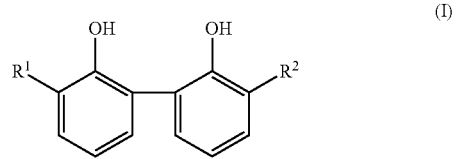

or a salt thereof, wherein $R^1$ and $R^2$ are each independently $(C_1-C_6)$ alkyl or $(C_2-C_6)$ alkenyl, and a carrier. In certain embodiments, the composition is an oral care composition that comprises an antibacterially-effective amount of a compound of Formula (I), or a salt thereof, and an orally-acceptable carrier. In other embodiments, the composition comprises an antibacterially-effective amount of a compound of Formula (I) or a salt thereof, and a dermatologically-acceptable carrier.

In certain embodiments, $R^1$ and $R^2$ are independently selected from methyl, ethyl, n-propyl, i-propyl, n-butyl, i-butyl, t-butyl, 2-methyl-butyl, n-pentyl, i-pentyl, t-pentyl and hexyl. In other embodiments, $R^1$ and $R^2$ are the same and both are $(C_1-C_6)$ alkyl or $(C_2-C_6)$ alkenyl.

In a particular embodiment, $R^1$ and $R^2$ are both n-propyl, and the compound of Formula (I) is compound (3), which has the following structure:

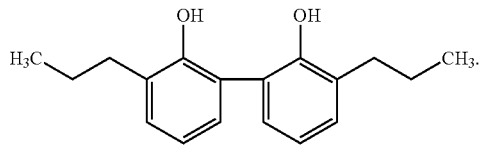 [SMILES: CCCc1cccc(-c2cccc(CCC)c2O)c1O]

Some embodiments provide a method of inhibiting bacterial growth in an oral cavity comprising contacting an oral cavity surface with any one of the compositions described herein. Other embodiments provide a method of treating or preventing a disease or condition of the oral cavity comprising contacting an oral cavity surface with any one of the compositions described herein. Still other embodiments provide a method of treating or preventing a disease or condition of the skin comprising contacting a skin surface of a subject in need thereof with any one of the compositions described herein.

DETAILED DESCRIPTION

As used throughout, ranges are used as shorthand for describing each and every value that is within the range. Any value within the range can be selected as the terminus of the range.

All references cited herein are hereby incorporated by reference in their entireties.

In the event of a conflict in a definition in the present disclosure and that of a cited reference, the present disclosure controls.

As used herein, the term "$(C_1-C_6)$ alkyl" refers to a substituted or unsubstituted saturated straight-chain aliphatic hydrocarbon of 1 to 6 carbon atoms, e.g. methyl, ethyl, n-propyl, i-propyl, n-butyl, n-pentyl, and hexyl. In some embodiments, the $(C_1-C_6)$ alkyl moiety is substituted with a halogen atom, e.g. fluorine, bromine or chlorine.

As used herein, the term "$(C_2-C_6)$ alkenyl" refers to an unsaturated, open chain hydrocarbon comprising from two to six carbon atoms with one or more carbon-carbon double bonds, having the general formula $C_nH_{2n}$, e.g. vinyl and propenyl.

Some embodiments of the present invention provide an oral or personal care composition comprising a compound of Formula (I):

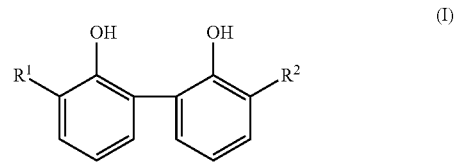

or a salt thereof; wherein: $R_1$ and $R_2$ are independently selected from $(C_1-C_6)$ alkyl and $(C_2-C_6)$ alkenyl, and a carrier. In some embodiments, the carrier is an orally acceptable carrier. In other embodiments, the carrier is a carrier suitable for a dermatologically-acceptable personal care composition.

Component, ingredients, and methods suitable for formulation of a dermatologically-acceptable personal care carrier are described, for example, in U.S. Patent Application Publication No. US 2007/0048235. Some embodiments provide a composition comprising any one of the compounds described herein. In some embodiments, the personal care composition is selected from: a soap (e.g. in bar or liquid form), a body wash, a gel, a lotion, an underarm product (e.g. a deodorant or antiperspirant), an ointment, and a cream.

In some embodiments, the present invention provides compositions wherein the compound of Formula (I) is present at a concentration of from about 0.001 to about 10%, by weight. Other embodiments provide compositions wherein the compound of Formula (I) is present at a concentration of from about 0.005 to about 7.5%, by weight. Other embodiments provide compositions wherein the compound of Formula (I) is present at a concentration of from about 0.01 to about 5%, by weight. Other embodiments provide compositions wherein the compound of Formula (I) is present at a concentration of from about 0.05 to about 3.5%, by weight. Other embodiments provide compositions wherein the compound of Formula (I) is present at a concentration of from about 0.1 to about 3.0%, by weight. Other embodiments provide compositions wherein the compound of Formula (I) is present at a concentration of from about 0.3 to about 1.0%, by weight. Still other embodiments provide compositions wherein the compound of Formula (I) is present at a concentration of about 0.5%, by weight. Another embodiment provides compositions wherein the compound of Formula (I) is present at a concentration of about 1.0%, by weight.

In some embodiments, the composition further comprises one or more components selected from a fluoride ion source; a tartar control agent; a buffering agent; an abrasive; and a combination of two or more thereof. In some embodiments, at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof. In addition to those disclosed herein, suitable humectants, thickeners, surfactants, colorants, and abrasives are disclosed in commonly-owned U.S. Published Patent Application No. 11/0059029 A1, U.S. Published Patent Application No. 2009/0311200 A1, and U.S. Published Patent Application No. 2008/0233058 A1.

Some embodiments provide a method of treating or preventing a disease or condition of the oral cavity comprising contacting an oral cavity surface with any one of the compositions described herein. In some embodiments, the disease or condition of the oral cavity includes a disease or condition of the teeth, oral mucosa, gingiva or tongue. In some embodiments, the disease or condition of the oral cavity is selected from caries, gingivitis, periodontitis, halitosis, and combination of two or more thereof.

In some embodiments, the present invention provides a method of treating or preventing a disease or condition of the skin comprising contacting the skin surface of a subject in need thereof with any one of the compositions described herein. In some embodiments, the disease or condition is selected from: body odor, erythrasma, acne, impetigo, boils, folliculitis, cellulitis, carbuncles, scalded skin syndrome, and a combination of two or more thereof.

In some embodiments, the method comprises repeating the application of the composition multiple times until the desired anti-bacterial effects are achieved in the subject. In some embodiments, the composition is applied daily for a period of several days, e.g. at least one week.

In some embodiments, the composition further comprises an active compound selected from: magnolol, tetrahydromagnolol, butyl magnolol, honokiol, tetrahydrohonokiol, triclosan, delmopinol, cetyl pyridinium chloride, a zinc ion source, a stannous ion source, an anti-inflammatory agent, a botanical agent, and a combination of two or more thereof. Suitable botanical agents include those disclosed in commonly-owned U.S. Patent Application Publication No. 2009/0087501 A1. Suitable anti-inflammatory agents include any orally acceptable anti-inflammatory agent, including steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone, phenylbutazone, and mixtures thereof.

Suitable carriers include the conventional and known carriers used in making toothpastes, tooth powders, prophylaxis pastes, mouth rinses, lozenges, gums, beads, strips, films, sprays and the like. As those skilled in the art will appreciate, the selection of specific carrier components is dependent on the desired product form, including toothpastes, tooth powders, prophylaxis pastes, mouth rinses, lozenges, gums, gels, paints, confectionaries, and the like.

In some embodiments, the oral composition further comprises one or more components selected from cleaning agents, flavoring agents, sweetening agents, anti-adhesion agents, surfactants, foam modulators, abrasives, pH modifying agents, humectants, moisturizers, mouth feel agents, colorants, abrasives, whitening agents, preservatives, a fluoride ion source, a saliva stimulating agent, emollients, viscosity modifiers, diluents, emulsifiers, nutrients and combinations thereof. Other optional additives may be included.

Colorants such as dyes may be food color additives presently certified under the Food Drug & Cosmetic Act for use in food and ingested drugs, including dyes such as FD&C Red No. 3 (sodium salt of tetraiodofluorescein), Food Red 17, disodium salt of 6-hydroxy-5-{(2-methoxy-5-methyl-4-sulphophenyl)azo}-2-n-aphthalenesulfonic acid, Food Yellow 13, sodium salt of a mixture of the mono and disulphonic acids of quinophtalone or 2-(2-quinolyl)indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-DELTA-3,5-cyclohexadienimine], FD&C Blue No. 1 (disodium salt of dibenzyldiethyl-diamino-triphenylcarbinol trisulfonic acid anhydrite), FD&C Blue No. 2 (sodium salt of disulfonic acid of indigotin) and mixtures thereof in various proportions. Typically, colorants if included are present in very small quantities.

Suitable flavoring agents include, but are not limited to, natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, peppermint oil, clove oil, bay oil, thyme oil, cedar leaf oil, oil of nutmeg, oil of sage, and oil of bitter almonds. These flavoring agents can be used individually or in admixture. Commonly used flavors include mints such as peppermint, artificial vanilla, cinnamon derivatives, and various fruit flavors, whether employed individually or in admixture. Generally, any flavoring agent or food additive, such as those described in Chemicals Used in Food Processing, publication 1274 by the National Academy of Sciences, pages 63-258, may be used. Typically, flavoring agents, if included, are present at a concentration of from about 0.01 to about 1%, by weight. In some embodiments, the flavoring agent may be present at a concentration of about 0.2%, by weight.

Sweeteners include both natural and artificial sweeteners. Suitable sweeteners include water soluble sweetening agents such as monosaccharides, disaccharides and polysaccharides such as xylose, ribose, glucose (dextrose), mannose, galactose, fructose (levulose), sucrose (sugar), maltose, water soluble artificial sweeteners such as the soluble saccharin salts, i.e., sodium or calcium saccharin salts, cyclamate salts dipeptide based sweeteners, such a L-aspartic acid derived sweeteners, such as L-aspartyl-L-phenylalaine methyl ester (aspartame). In general, the effective amount of sweetener is utilized to provide the level of sweetness desired for a particular composition, will vary with the sweetener selected. This amount will normally be from about 0.001 to about 5%, by weight. In some embodiments, the sweetener is sodium saccharin and is present at a concentration of about 0.01%, by weight.

Whitening agents, material which is effective to effect whitening of a tooth surface to which it is applied, such as hydrogen peroxide and urea peroxide, high cleaning silica, preservatives, silicones, and chlorophyll compounds may be incorporated into the compositions of the present invention. In various embodiments, the compositions of this invention comprise a peroxide whitening agent, comprising a peroxide compound. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. One or more whitening agents are optionally present in a tooth-whitening effective total amount. In some embodiments the whitening agent is separated from the aqueous carrier. In some embodiments the whitening agent is separated from the aqueous carrier by encapsulation of the whitening agent.

Optionally, breath freshening agents may be provided. Any orally acceptable breath freshening agent can be used, including without limitation zinc salts such as zinc gluconate, zinc citrate, zinc oxide and zinc chlorite, alpha-ionone and mixtures thereof. One or more breath freshening agents are optionally present in a breath freshening effective total amount.

Optionally, the composition may include a tartar control (anticalculus) agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J. In some embodiments, a phosphate is present at a concentration of from about 0.01 to about 10%, by weight. In some embodiments, a phosphate is present at a concentration of from about 1%, by weight.

Some embodiments provide compositions wherein a buffering agent is present. In some embodiments, sodium phosphate monobasic is present at a concentration of from about 0.01 to about 5%, by weight. In some embodiments, sodium phosphate monobasic phosphate is present at a concentration of about 1%, by weight. In some embodiments, sodium phosphate dibasic is present at a concentration of from about 0.01 to about 5%, by weight. In some embodiments, sodium phosphate dibasic phosphate is present at a concentration of about 0.15%, by weight.

Other optional additives include antimicrobial (e.g., antibacterial) agents. Any orally acceptable antimicrobial agent can be used, including Triclosan (5-chloro-2-(2,4-dichlorophenoxy)phenol); 8-hydroxyquinoline and salts thereof, zinc and stannous ion sources such as zinc citrate, zinc sulfate and zinc gluconate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethylpyridinium chloride); biguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; grapeseed extract; thymol; eugenol; menthol; geraniol; carvacrol; citral; eucalyptol; catechol; 4-allylcatechol; hexyl resorcinol; methyl salicylate. A further illustrative list of useful antibacterial agents is provided in U.S. Pat. No. 5,776,435, Gaffar, et al., issued Jul. 7, 1998. In some embodiments, the antimicrobial agent is present at a concentration of from about 0.001 to about 1%, by weight. In some embodiments, the antimicrobial agent is cetylpyridinium chloride. In some embodiments, cetylpyridinium chloride is present at a concentration of from about 0.001 to about 1%, by weight. In other embodiments, cetylpyridinium chloride is present at a concentration of about 0.05%, by weight.

Abrasives are another class of optional additives. Suitable abrasives include without limitation, silica, for example in the form of silica gel, hydrated silica or precipitated silica, amorphous silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calciumpyrophosphate, tricalcium phosphate, calcium polymetaphosphate and insoluble sodium polymetaphosphate.

Antioxidants are another class of optional additives. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Also optional, a saliva stimulating agent, useful for example in amelioration of dry mouth, may be included. Any orally acceptable saliva stimulating agent can be used, including without limitation food acids such as citric, lactic, malic, succinic, ascorbic, adipic, fumaric, and tartaric acids, and mixtures thereof. One or more saliva stimulating agents are optionally present in a saliva stimulating effective total amount.

Optionally, an antiplaque (e.g., plaque disrupting) agent may be included. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and mixtures thereof.

Optional desensitizing agents include potassium citrate, potassium chloride, potassium tartrate, potassium bicarbonate, potassium oxalate, potassium nitrate, strontium salts, and mixtures thereof.

Optional additives also include vitamins, herbs and proteins. Vitamins include Vitamins C and D, thiamine, riboflavin, calcium pantothenate, niacin, folic acid, nicotinamide, pyridoxine, cyanocobalamin, para-aminobenzoic acid, bioflavonoids, pantheon, retinyl palmitate, tocopherol acetate, and mixtures thereof. Herbs such as *Chamomilla recutita, Mentha piperita, Salvia officinalis*, and *Commiphora myrrha* may optionally be included. Suitable proteins include milk proteins and enzymes such as peroxide-producing enzymes, amylase, plaque-disrupting agents such as papain, glucoamylase, and glucose oxidase.

*S. aureus* can cause a range of illnesses from minor skin infections, such as pimples, impetigo, boils, cellulitis, carbuncles, scalded skin syndrome, and abscesses, to life threatening diseases such as pneumonia, meningitis, osteomyelitis, endocarditis, toxic shock syndrome, and sepsis. *S. aureus* is also often responsible for nosocomial infections.

*C. minutissimum* and *C. xerosis* are known to be involved in the generation of body odor. *C. minutissimum* is also associated with erythrasmas.

Embodiments of the present invention are further described in the following examples. The examples are merely illustrative and do not in any way limit the scope of the invention as described and claimed.

EXAMPLES

Example 1

Compounds of the present invention can be prepared generally according to methods disclosed by Alexakis (Alexakis et al., *J. Org. Chem.* 69: 5660-5667 (2004)), or according to methods known to those skilled in the art.

Example 2

Table 1 (below) describes the antibacterial efficacy (Minimum Inhibitory Concentration test) of Compound (3)

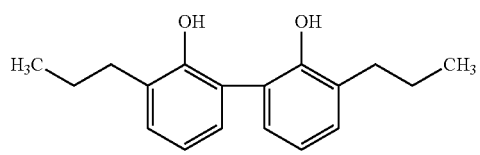 [SMILES: CCCc1cccc(-c2cccc(CCC)c2O)c1O]

which is an exemplary compound of the present invention, against common oral bacteria, *A. viscosus, S. mutans, S. oralis, S. sanguis*, and *L. casei*.

Minimum Inhibitory Concentration values are determined generally according to the following method: A series of two-fold dilutions of compound (3) in trypticase soy broth (Catalog No. 211768; Becton Dickinson, Franklin Lakes N.J.) was prepared in a 96 well plate and a constant amount of bacteria was then added to each well. After 18-24 hours of incubation, bacterial growth was measured with a Spectrophotometric Micro-plate Reader (Powerwave 5x, BioTEK, Winooski Vt.) and the MIC values were determined Results are provided in Table 1:

TABLE 1

| Bacterium | Minimum Inhibitory Concentration (ppm) Compound (3) [1,1-Biphenyl]-,2'-diol,3,3'-dipropyl |
|---|---|
| *A. viscosus* | 3.9 |
| *S. sanguis* | 3.9 |
| *S. mutans* | 7.8 |
| *S. oralis* | 7.8 |
| *L. casei* | 7.8 |

The results shown in Table 1 demonstrate that compound (3), [1,1-Biphenyl]-2,2'-diol,3,3' dipropyl, has antibacterial activity.

Example 3

Formulations comprising compound (3) and magnolol were prepared as indicated below.

The composition of three illustrative liquid formulations A, B, and C, are set forth in Table 2, below:

TABLE 2

|  | A | B | C |
|---|---|---|---|
| Part 1 |  |  |  |
| Compound (3) (%) | 1.33 | 1.33 |  |
| Magnolol (%) |  |  | 1.33 |
| Polyethylene glycol 600 (%) | 2.67 | 4 | 4 |
| Flavor (%) | 1.33 | 1.33 | 1.33 |
| Propylene glycol manocaprylate (%) | 1.33 |  |  |
| Part 2 |  |  |  |
| Glycerin (%) | 24 | 24 | 24 |
| Sorbitol - 70% aqueous solution (%) | 24 | 24 | 24 |
| Sodium saccharin (%) | 0.4 | 0.4 | 0.4 |
| Sodium fluoride (%) | 0.324 | 0.324 | 0.324 |
| Sodium lauryl sulfate (%) | 2.4 | 2.4 | 2.4 |
| Water (%) | 42.206 | 42.206 | 42.206 |

The composition of an additional five illustrative liquid formulations, designated D-H, are set forth in Table 3, below

TABLE 3

|  | D | E | F | G | H |
|---|---|---|---|---|---|
| Part 1 |  |  |  |  |  |
| Compound (3) (%) | 1.33 |  | 1.33 |  |  |
| Magnolol (%) |  |  |  |  | 1.33 |
| Polyethylene glycol 600 (%) | 2.67 | 2.67 | 2.67 | 2.67 | 4 |
| Flavor (%) | 1.33 | 1.33 | 1.33 | 1.33 | 1.33 |
| Propylene glycol monolaurate (%) | 1.33 | 1.33 |  |  |  |
| Propylene glycol manocaprylate (%) |  |  |  | 1.33 | 1.33 |

TABLE 3-continued

|  | D | E | F | G | H |
|---|---|---|---|---|---|
| Part 2 |  |  |  |  |  |
| Glycerin (%) | 24 | 24 | 24 | 24 | 24 |
| Sorbitol - 70% aqueous solution (%) | 24 | 24 | 24 | 24 | 24 |
| Sodium saccharin (%) | 0.4 | 0.4 | 0.4 | 0.4 | 0.4 |
| Sodium fluoride (%) | 0.324 | 0.324 | 0.324 | 0.324 | 0.324 |
| Sodium lauryl sulfate (%) | 2 | 2 | 2.4 | 2.4 | 2.4 |
| Water (%) | QS | QS | QS | QS | QS |

The composition of four additional, illustrative liquid formulations, designated I-L, are set forth in Table 4, below

TABLE 4

|  | I | J | K | L |
|---|---|---|---|---|
| Part 1 |  |  |  |  |
| Compound (3) (%) | 0.4 | 0.67 | 0.93 | 1.33 |
| Polyethylene glycol 600 (%) | 4 | 4 | 4 | 4 |
| Flavor (%) | 1.33 | 1.33 | 1.33 | 1.33 |
| Part 2 |  |  |  |  |
| Glycerin (%) | 24 | 24 | 24 | 24 |
| Sorbitol - 70% aqueous solution (%) | 24 | 24 | 24 | 24 |
| Sodium saccharin (%) | 0.4 | 0.4 | 0.4 | 0.4 |
| Sodium fluoride (%) | 0.324 | 0.324 | 0.324 | 0.324 |
| Sodium lauryl sulfate (%) | 2.4 | 2.4 | 2.4 | 2.4 |
| Water (%) | QS | QS | QS | QS |

Liquid formulations A-L are prepared in the following manner. All of the ingredients of Part 1 are mixed to provide a clear solution. Separately, the ingredients of Part 2 are combined with one another. The first mixture, Part 1, is then added to the mixture of Part 2, with continuous agitation to provide the liquid composition.

The compositions of six toothpaste formulations, designated M-R, are provided below in Table 5.

Toothpaste formulations M-R are prepared in the following manner. Part 2, is premixed by combining the sodium saccharine and sodium fluoride in water. The gel phase (Part 1) is prepared separately by dispersing the CMC (carboxymethylcellulose), xanthan gum, and titanium dioxide in glycerin. The dispersion is mixed for five minutes after which the sorbitol is added with continuous agitation, and then mixed for five minutes. Part 3 is prepared by combining all of the listed ingredients, which are mixed well to provide a clear solution. Part 2 is added to Part 1 (the gel phase) and mixed for ten minutes and the combined mixture transferred to a suitable mixer (e.g., a vacuum equipped, double planetary mixer, Charles Ross & Son Company, Hauppauge, N.Y.). The components of Part 4, (the amorphous silica abrasive, amorphous silica thickener, and high cleaning silica) are added and wetted, and then mixed for twenty minutes at high speed under full vacuum. Part 3 and Part 5 (sodium lauryl sulfate) are added and mixed for ten minutes at low speed under full vacuum.

Example 4

Compound (3) was evaluated for its antibacterial efficacy against representative skin bacteria such as *Staphylococcus aureus* (*S. aureus*), *Corynebacterium minutissimum* (*C. minutissimum*), and *Escherichia coli* (*E. coli*). Minimum Inhibitory Concentration (MIC), and a Short Interval Kill Test (SIKT) were performed, and the results are described in Table 6 and Table 7 (below).

A. Minimum Inhibitory Concentration (MIC)

MIC values against three common skin bacteria were determined for Compound (3) using the following method: A series of two-fold dilutions of Compound (3) was prepared in a 96 well plate and a constant amount of bacteria was added to each well. After 18-24 hours of incubation, bacterial growth was measured with a Spectrophotometric Micro-plate Reader and the MIC values were determined. Results are provided in Table 6 (below):

TABLE 5

|  | M | N | O | P | Q | R |
|---|---|---|---|---|---|---|
| Part 1 |  |  |  |  |  |  |
| Glycerin (%) | 18 | 18 | 18 | 18 | 18 | 18 |
| Xanthan Gum (%) | 0.4 | 0.4 | 0.4 | 0.4 | 0.4 | 0.4 |
| Sodium CMC (%) | 1.1 | 1.1 | 1.1 | 1.1 | 1.1 | 1.1 |
| Titanium dioxide (%) | 0.5 | 0.5 | 0.5 | 0.5 | 0.5 | 0.5 |
| Sorbitol - 70% Solution (%) | 17.8 | 17.8 | 17.8 | 17.8 | 17.8 | 17.8 |
| Part 2 |  |  |  |  |  |  |
| Deionized water | QS | QS | QS | QS | QS | QS |
| Sodium fluoride (%) | .243 | .243 | .243 | .243 | .243 | .243 |
| Sodium saccharide (%) | 3 | 3 | 3 | 3 | 3 | 3 |
| Part 3 |  |  |  |  |  |  |
| Polyethylene glycol 600 (%) | 3 | 3 | 3 | 3 | 3 | 3 |
| Magnolol (%) | 1 |  |  |  |  |  |
| Compound (3) (%) |  | 0.3 | 0.5 | 0.7 | 1 |  |
| Flavor (%) | 1 | 1 | 1 | 1 | 1 | 1 |
| Part 4 |  |  |  |  |  |  |
| Amorphous silica - abrasive | 8.5 | 8.5 | 8.5 | 8.5 | 8.5 | 8.5 |
| Amorphous silica - thickener | 3 | 3 | 3 | 3 | 3 | 3 |
| High cleaning silica | 10 | 10 | 10 | 10 | 10 | 10 |
| Part 5 |  |  |  |  |  |  |
| Sodium lauryl sulfate (%) | 1.8 | 1.8 | 1.8 | 1.8 | 1.8 | 1.8 |

TABLE 6

| Bacterium | Minimum Inhibitory Concentration (ppm) |
|---|---|
| E. coli | 62.5 |
| S. aureus | 31.25 |
| C. minutissimum | 62.5 |

The results presented in Table 6 (above) further demonstrate the anti-bacterial efficacy of Compound (3), a compound of Formula (I), against common skin bacteria.

B. Short Interval Kill Test (SIKT)

The SIKT test determines the kill effect of a test compound at a predetermined exposure time. The SIKT values presented below in Table 7, were obtained generally according to the following method: An aliquot of Compound (3) in a volume of 1.2 mL is transferred into a sterile test tube, to which 0.2 mL of a freshly prepared bacterial suspension (OD adjusted to 0.1 at 620 nm) is added and gently mixed. The reaction is neutralized at the 1 minute point by adding a neutralizing broth. The resulting mixture is then further diluted (serial ten-fold dilutions) with Letheen broth and an aliquot of each dilution is plated on MCA (Microbial Count Agar) plates for viable bacterial count. The results are provided in Table 7 (below).

TABLE 7

| Test Bacterium | SIKT (% Reduction in viable count in 1 min.) |
|---|---|
| E. coli | 99.55 |
| S. aureus | 99.99 |

The data presented in Table 7 (above) provide further evidence of the antibacterial efficacy of Compound (3), an illustrative compound of Formula (I).

Example 5

The antibacterial efficacy of the Compound (3), an illustrative compound of Formula (I) was also evaluated in an instant killing assay involving determination of metabolic activity of cells using a redox dye, AlamarBlue® generally according to the manufacturer's instructions (Invitrogen, Carlsbad, Calif.). The dye, AlamarBlue® is a redox indicator that yields a colorimetric change and a fluorescent signal in a response to metabolic activity. The principle underlying this assay is the ability of metabolically-active cells to convert the dye (AlamarBlue®) into a fluorescent derivative with reduce light absorption at 590 nm. The assay was carried out generally according to the following procedure: A 200μ sample of a culture of A. viscous ($OD_{610}$ 0.5-1.0) is aliquoted into each well of a 96-well plate. Samples of formulations comprising Compound (3) are prepared as slurries generally as follows: tooth paste formulations are diluted 1:4 with deionized water while liquid dentifrices are diluted 0.75:4 with deionized water. A 2.5 μl of each slurry is added to each well already containing the aliquoted bacterial culture. After 2.5 minutes, a 20 μl aliquot of a solution of AlamarBlue® dye is added and incubation continued for a period of time sufficient to allow color development, i.e., about 10 to 20 minutes, after which the untreated control becomes pink. The plates are then centrifuged, the supernatant is recovered and transferred to a second 96 well plate and the optimal density each sample at 590 nm is determined ($OD_{590}$). In this assay, actively metabolizing cells convert the blue dye to a pink fluorescent derivative, with a resulting decrease in optical density at 590 nm. Non-viable, non-metabolizing cells, in contrast, are less able or unable to mediate this conversion, thereby minimizing the loss of optical density at 590 nm. Accordingly, higher $OD_{590}$ values in Table 8, below, indicate cell killing. The compositions of each of Formulations A-C are provided in Table 2, while those for Formulations M and Q are provided in Table 5 above.

TABLE 8

| | $OD_{590}$ | | | | | | |
|---|---|---|---|---|---|---|---|
| | Untreated | Form. A | Form. B | Form. C | Form. M | Form. Q | Untreated |
| Well 1 | 0.055 | 0.165 | 0.172 | 0.177 | 0.187 | 0.197 | 0.072 |
| Well 2 | 0.079 | 0.271 | 0.292 | 0.265 | 0.222 | 0.218 | 0.08 |
| Well 3 | 0.086 | 0.214 | 0.244 | 0.226 | 0.226 | 0.208 | 0.089 |
| Well 4 | 0.094 | 0.231 | 0.242 | 0.244 | 0.241 | 0.218 | 0.083 |
| Average | 0.079 | 0.220 | 0.238 | 0.228 | 0.219 | 0.210 | 0.081 |
| Std. Dev | 0.017 | 0.044 | 0.049 | 0.038 | 0.023 | 0.010 | 0.007 |

The data described in Table 8 demonstrate that Compound (3), when formulated both as a liquid composition (Formulations A and B), and as a toothpaste (Formulation Q) exhibited efficacy comparable to that of magnolol, formulated as a liquid (Formulation C) and as a toothpaste (Formulation M).

Example 6

Prostaglandin $E_2$ ($PGE_2$) is a key mediator of periodontal inflammation and its expression is a well-established as a biomarker associated with gingival inflammation. As demonstrated below, Compound (3) has a substantial anti-inflammatory activity. The data of Table 9 were obtained generally according to the following method: A 100 μL aliquot of DMEM media (Dulbecco's Modified Eagle Medium) (Invitrogen, Carlsbad, Calif.) containing either IL-1β (10 ng/ml) (Roche Applied Science, Indianapolis Ind.) or $10^8$ heat-killed Prophynomonas gingivalis (HKPG) into each well of a sterile 96-well plate ("mirror plate"). An additional 98 μl aliquot of DMEM media containing either IL-1β or HKPG was added to the first well in each row. In the next step, 0.4 μL of a 1% stock the compound to be tested was added to the first well of each row, and then serial dilutions (using 100 μl from each well) were made, starting from the first well and proceeding across plate. After the serial dilutions have been made, an additional 100 μL media containing either IL-1β or HKPG was added to each well. Accordingly, the first well of each row contains 200 μL of a 10 ppm solution of the test compound, which is diluted by a factor of two as one moves across the row of the plate. A negative control is introduced using 200 μL of media without IL-1β, HKPG, or a test compound, and a positive control is introduced using 200 μL of media containing IL-1β or HKPG but no test compound.

Each well of a second plate containing growing cells (human embryo palatal mesenchyme cells, catalog no. CRL-1486; ATCC, Manassas, Va.) is washed twice with PBS, after which any remaining media is aspirated from the wells. Media from the "mirror plate" is transferred to the plate carrying the grown cells. After an overnight incubation, a 70 μL aliquot is removed from each well and transferred to an assay plate of a $PGE_2$ EIA assay kit. An additional 30 μL aliquot of media is added to each well to adjust the final volume to 100 μL and the level of PGE$_2$ determined using a detection kit generally according to the manufacturer's instructions (PEG2-EIA Kit, catalogue no. 901-001; Assay Designs Inc, Ann Arbor Mich.) and software (GraphPad Prism, GraphPad Software, Inc., San Diego Calif.). The data (IC$_{50}$) obtained are presented in Table 9, below:

TABLE 9

|  | IC$_{50}$ (ppm) |
| --- | --- |
| Compound (3) | 0.25 |
| Magnolol | 0.40 |

The data of Table 9 demonstrate that Compound (3) has anti-inflammatory activity.

Example 7

Table 10 (below) provides the formulation of an exemplary oral care composition of the present invention, employing Compound (3), an illustrative representative of the compounds of Formula (I).

TABLE 10

| Ingredient | % w/w |
| --- | --- |
| Water | 30 |
| Sorbitol | 30 |
| Glycerin | 15 |
| Zeodent 114 | 11 |
| Zeodent 105 | 10 |
| Sodium carboxymethylcellulose | 1.1 |
| Flavor | 1 |
| Titanium dioxide | 0.5 |
| Compound (3) | 0.5 |
| Carrageenan | 0.4 |
| Sodium saccharin | 0.3 |
| Sodium fluoride | 0.24 |

The formulation described in Table 10 (above) can be prepared by methods known in the art. An exemplary method is provided below.

Two premixes can be made. Sodium saccharin, sodium sulfate and fluoride are dissolved in water to form premix 1. The compound of Formula (I), i.e., Compound (3) is added to the flavor component and mixed until dissolved or dispersed, to form premix 2. Gums (carboxymethyl cellulose and carrageenan) and titanium dioxide are dispersed in glycerin and mixed for 5 minutes. Sorbitol is added and the combination is mixed for an additional 5 minutes. The resultant mixture comprises a gel phase. Premix 1 is then added to the gel phase, and mixed for about 5 minutes. The gel phase is transferred to a Ross mixer, where the silicas are added and mixed for about 20 minutes at high speed with vacuum. Premix 2 and sodium lauryl sulfate is then added to the Ross mixer, wherein the combination is wet mixed for about 10 minutes at low speed with vacuum.

Example 8

The compositions described in Table 11 (below) can be prepared according to known methods for preparing personal care compositions, for example, those described in U.S. Patent Application Publication No. 2007/0048235. Table 11 provides the formulation of an exemplary liquid soap composition of the present invention employing Compound (3), an illustrative representative of the compounds of Formula (I).

TABLE 11

| Ingredient | % w/w |
| --- | --- |
| Water | 68.3 |
| Sodium alpha olefin sulfonate | 22.3 |
| Lauramide DEA | 3.1 |
| Cocoamidopropyl betaine | 3.1 |
| Sodium chloride | 0.6 |
| Polyquaternium-7 | 1 |
| DMDM Hydatoin | 0.4 |
| Fragrance | 0.3 |
| Citric acid | 0.3 |
| Compound (3) | 0.5 |
| Tetrasodium EDTA | 0.1 |
| Aloe vera gel | 0.01 |
| Glycerin | 0.01 |

As those skilled in the art will appreciate, numerous changes and modifications may be made to the embodiments described herein without departing from the spirit of the invention. It is intended that all such variations fall within the scope of the appended claims.

What is claimed is:

1. An oral care composition comprising
   an antibacterially-effective amount of a compound of Formula (I)
   having the following structure:

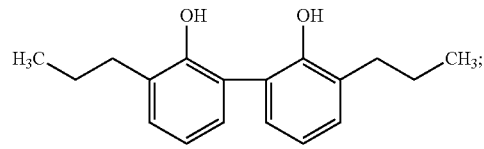 [SMILES: CCCc1cccc(-c2cccc(CCC)c2O)c1O]

and an orally-acceptable carrier.

2. The oral care composition of claim 1, wherein the compound of Formula (I) is present at a concentration of from about 0.001% to about 10%, by weight.

3. The oral care composition of claim 1, wherein the compound of Formula (I) is present at a concentration of from about 0.01% to about 5%, by weight.

4. The oral care composition of claim 1, wherein the compound of Formula (I) is present at a concentration of from about 0.1% to about 2.5%, by weight.

5. The oral care composition of claim 1, further comprising an active agent selected from the group consisting of magnolol, tetrahydromagnolol, butyl magnolol, honokiol, tetrahydrohonokiol, triclosan, delmopinol, cetyl pyridinium chloride, a zinc ion source, a stannous ion source, an anti-inflammatory agent, a botanical agent, and a combination of two or more thereof.

6. The oral care composition of claim 1, wherein the oral care composition is selected from the group consisting of a tooth paste, a gel, a mousse, a powder, a confectionary, a strip, an oral spray and a mouth rinse.

7. The oral care composition of claim 1, wherein the oral care composition is a tooth paste comprising a component selected from the group consisting of a humectant, an abrasive, a fluoride ion source, an anticalculus agent, a buffering agent, a thickener, a cleaning agent, a whitener, and a combination of two or more thereof.

8. The oral care composition of claim 7, wherein the fluoride ion source is selected from the group consisting of stannous fluoride, sodium fluoride, potassium fluoride, sodium monofluorophosphate, sodium fluorosilicate, ammonium fluorosilicate, amine fluoride, ammonium fluoride, and a combination of two or more thereof.

9. The oral care composition of claim 7, wherein the anticalculus agent is selected from the group consisting of tetrasodium pyrophosphate, trisodium pyrophosphate, a synthetic anionic polycarboxylate, and a combination of two or more thereof.

10. The oral care composition of claim 7, wherein the abrasive is an amorphous silica abrasive.

11. The oral care composition of claim 7, wherein the thickener is an amorphous silica thickener.

12. The oral care composition of claim 7, wherein the cleaning agent is a high cleaning silica.

13. A method for inhibiting bacterial growth in an oral cavity of a subject in need thereof, the method comprising contacting an oral cavity surface of the subject with a composition comprising a compound of formula (I) having the following structure:

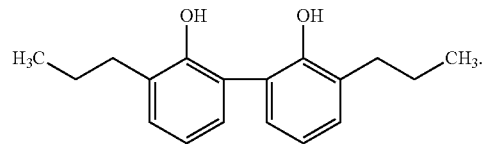 [SMILES: CCCc1cccc(-c2cccc(CCC)c2O)c1O]

14. A personal care composition comprising an antibacterially-effective amount of a compound of formula (I) having the following structure:

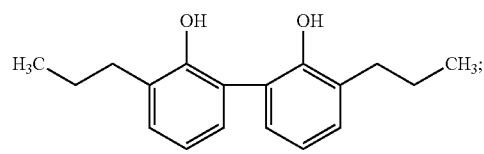 [SMILES: CCCc1cccc(-c2cccc(CCC)c2O)c1O]

and a dermatologically-acceptable carrier.

15. A method of treating a skin condition in a subject in need thereof, comprising contacting the skin of the subject with the composition of claim 14.

16. The method of claim 15, wherein the condition is selected from the group consisting of body odor, eryhthrasma, acne, impetigo, boils, folliculitis, cellulitis, carbuncles, and scalded skin syndrome.

* * * * *